(12) United States Patent  (10) Patent No.: US 8,026,108 B1
Huo et al.  (45) Date of Patent: Sep. 27, 2011

(54) DETECTION OF BIOTARGETS USING BIORECEPTOR FUNCTIONALIZED NANOPARTICLES

(75) Inventors: Qun Huo, Orlando, FL (US); Xiong Liu, Oviedo, FL (US); Qiu Dai, Orlando, FL (US)

(73) Assignee: The University of Central Florida Research Foundation, Inc., Orlando, FL (US)

( * ) Notice: Subject to any disclaimer, the term of this patent is extended or adjusted under 35 U.S.C. 154(b) by 425 days.

(21) Appl. No.: 11/875,252

(22) Filed: Oct. 19, 2007

Related U.S. Application Data

(60) Provisional application No. 60/862,125, filed on Oct. 19, 2006, provisional application No. 60/887,889, filed on Feb. 2, 2007.

(51) Int. Cl.
*G01N 21/00* (2006.01)
*G01N 33/53* (2006.01)
*G01N 33/536* (2006.01)
*G01N 33/553* (2006.01)

(52) U.S. Cl. .................... 436/525; 422/68.1; 422/82.05; 422/82.07; 422/82.08; 422/101; 435/4; 435/6; 435/7.1; 435/7.2; 435/7.92; 435/287.2; 435/288.7; 436/518; 436/523; 436/164; 436/172

(58) Field of Classification Search ................. None
See application file for complete search history.

(56) References Cited

U.S. PATENT DOCUMENTS

2005/0148005 A1* 7/2005 Emadi-Konjin et al. ......... 435/6
2005/0170352 A1* 8/2005 Chan et al. ....................... 435/6

FOREIGN PATENT DOCUMENTS

WO WO 2004016160 A2 * 2/2004
WO WO 2004045552 A2 * 6/2004

* cited by examiner

*Primary Examiner* — Unsu Jung
(74) *Attorney, Agent, or Firm* — Jetter & Associates, P.A.

(57) ABSTRACT

An ultra sensitive method for detection of biomolecules includes the step of providing a plurality of bioreceptor functionalized nanoparticle probes. The nanoparticles can include metal, semiconductor, radioactive isotope or fluorescent dye molecules. A sample solution suspected of including the target is contacted with the probes, wherein if present, the target binds to the bioreceptor. After such binding a separating step follows. In the separating step, probes having the target bound thereto are separated from probes not having the target bound thereto. In one embodiment probes having the target bound thereto are then decomposed to generate ions, or broken into discrete radioactive isotopes or fluorescent dye molecules to form a solution including a large plurality of metal ions, radioactive isotopes or dye molecules. A concentration of ions, radioactive isotopes, or dye molecules in the solution is then determined and using this information the concentration of the target in the original sample solution is determined.

14 Claims, 4 Drawing Sheets

DETECTION OF BIOTARGETS USING BIORECEPTOR FUNCTIONALIZED NANOPARTICLES

CROSS-REFERENCE TO RELATED APPLICATIONS

The present application incorporates by reference in its entirety and claims priority to U.S. Provisional Patent Application Ser. No. 60/862,125 filed Oct. 19, 2006, entitled "Ultra Sensitive Detection of Biotargets Using Ions, Discrete Radioactive Isotopes or Discrete Fluorescent Dye Molecules Derived from Bioreceptor Functionalized Nanoparticles" and U.S. Provisional Patent Application Ser. No. 60/887,889 filed Feb. 2, 2007, entitled "Ultra Sensitive Detection of Biotargets Using Ions, Discrete Radioactive Isotopes or Discrete Fluorescent Dye Molecules Derived from Bioreceptor Functionalized Nanoparticles".

STATEMENT REGARDING FEDERALLY SPONSORED RESEARCH OR DEVELOPMENT

The U.S. Government may have certain rights to the invention based on National Science Foundation Career Award DMR 0552295, and DMI 0506531.

FIELD OF THE INVENTION

The present invention relates to systems and methods of detecting biotargets using bioreceptor functionalized nanoparticles.

BACKGROUND OF THE INVENTION

Many medical diagnosis processes are based on the detection of biomarker molecules such as proteins, antibodies, enzymes, DNA or RNA that are often uniquely associated with a particular disease. When diseases such as cancer appear in a human body, the human body is known to produce levels of certain chemicals that are much lower, or non-existent, in a healthy human being. For example, the diagnosis of prostate cancer is initially based on the concentration of a protein called PSA in the body. When the concentration of PSA exceeds a certain normal range, the doctor will generally suggest other more direct tools such as biopsy and imaging techniques to confirm the diagnosis of prostate cancer. Another example is breast cancer. Breast cancer patients are known to have much higher level of a certain enzyme called carbonic anhydrase. The detection of an unusually high level of this enzyme can provide the initial tool for breast cancer diagnosis.

The accurate detection of biomolecules at extremely low levels is vital for early diagnosis of diseases. Regarding many cancers and other diseases, if diagnosed early, the chance for successful cure or treatment is much higher than being diagnosed at later stages. Enormous research efforts have been and are continuously being pursued toward techniques and tools for biomolecule detection at ultra low levels. For example, enzymes, fluorescent dye molecules, and radioactive isotopes have been used extensively for bioconjugation and bioassays. Among the different biolabels, fluorescent dye molecules have received much attention due to the high sensitivity common to fluorescence detection. Although fluorescent dye molecules display shortcomings such as photobleaching, instability, and sensitivity to environmental conditions such as pH variation, some of these problems are being overcome by introducing highly luminescent and photostable quantum dots and nanoparticles. Quantum dots have high quantum yields, high molar extinction coefficients, high resistance to photobleaching and exceptional resistance to photo- and chemical degradation. Due to these exceptional optical properties, quantum dots have become one of the most interesting materials for bioimaging, labeling, and sensing. Other types of nanoparticle materials, such as gold and silver, exhibit some other unique size-dependent optical properties such as surface plasmon resonance (SPR). The extinction coefficient of metal nanoparticles is orders of magnitude higher than typical organic molecules; therefore, low concentration detection of DNAs based on color change of gold nanoparticle-DNA probe conjugates has been developed. Another important optical property of metal nanoparticles, the surface enhanced Raman scattering, is also being studied for ultra low level detection of biomolecules.

In addition to the development of labeling materials that can lead to lower detection limit, new techniques and methodologies to concentrate the analyte molecules and/or amplify the analyte concentration have also been reported. An example of this approach is the barcode detection of proteins and DNAs using gold nanoparticles and magnetic microparticles developed by Mirkin et al. (Nam, J; Park, S.; Mirkin, C. A. "Bio-barcodes based on oligonucleotide-modified nanoparticles" *J. Am. Chem. Soc.* 2002, 124, 3820) The magnetic microparticles are used as a tool to concentrate analyte molecules in solution by applying magnetic field. To detect the analyte molecules, multiple bar code DNA molecules are attached to the gold nanoparticle that is conjugated to the detector molecule. The detection of the analyte molecule is realized indirectly by measuring the amount of the bar code DNA molecules attached to gold nanoparticles. To increase the detection limit, the concentration of DNA barcode can be increased by PCR amplification. Using the bio-barcode method, Mirkin et al. has achieved detection limits for DNA molecules at the attomolar range ($10^{-18}$ M) or lower. Similar approach has been demonstrated to detect prostate specific antigens (PSA) at attomolar concentration. Another extensively explored research area for protein detection is the use of DNA aptamers and PCR amplification technique. Specific binding towards a target protein is created by simultaneous binding of two DNA aptamers to two different sites of the same protein. Ligation of the two-closely positioned DNA aptamers followed by PCR amplification can lead to detection of target proteins at a level as low as zeptomole ($10^{-21}$) range.

Despite significant progress, there is a strong and urgent need to develop more sensitive, reliable and low cost techniques for biomolecular detection and analysis at ultra low level. Although the bar-code method developed by Mirkin et al. has pushed the detection limit beyond the attomolar range, this method involves the use of expensive biomolecules (DNA) and rather sophisticated procedures and analytical instrumentation. Moreover, the amplification effect of the bar-code method is limited to the number of DNA barcodes that can be attached to the nanoparticle surface.

Regarding the fluorescence detection technique, the fluorescence of organic dyes and quantum dots is often affected by the chemical environment of the sample solution, and such effect could be further manifested at ultra low concentration. Although surface enhanced Raman scattering has shown promising potential for label-free trace detection of biomolecules, the Raman enhancement effect is not well understood and further study is needed before a routine assay method can be developed from this effect. For the DNA aptamer ligation method, the biggest problem is that PCR amplification is needed for the analysis and the type of proteins that can be detected using this method is relatively limited.

Therefore, a facile and economic method that allows the detection of a wide range of biomarker and other biologically significant target molecules at ultra low concentration is needed preferably in a quantitative manner.

SUMMARY OF THE INVENTION

This Summary is provided to comply with 37 C.F.R. §1.73, requiring a summary of the invention briefly indicating the nature and substance of the invention. It is submitted with the understanding that it will not be used to interpret or limit the scope or meaning of the claims.

A method for detection of biomolecule targets that includes the steps of: providing a plurality of bioreceptor functionalized nanoparticles to act as probes of the target; contacting a sample solution suspected of including the targets with the probes where any targets in the sample solution bind to the probes; separating the probes into a first group of probes bound to targets and a second group of probes without bound targets; and breaking down the probes in one group or separately breaking down the probes in both groups, to release a plurality of signal moieties forming at least one signal moiety solution; measuring a parameter of the signal moieties in the signal moiety solutions; and determining a presence of targets in the sample solution from the measured parameter. The nanoparticles can be composed of metal, semiconductor, radioactive isotopes or fluorescent dye molecules and the bioreceptor is adapted for binding the probes to the targets where the nanoparticles of the probes in a separated group of probes can be broken down to a plurality of ions, discrete radioactive isotopes or discrete fluorescent dye molecules. When the nanoparticles are a metal the breaking down step is the oxidation of the metal to metal ions. Metals that can be used include gold, silver, cadmium or an alloy thereof. The bioreceptor can be an antibody, DNA, proteins including enzymes, cells or cell components that bind strongly to a biomolecular targets which can be one or more biomarkers of at least one type of cancer. The sample solution can be a bodily fluid or a fluid derived from body tissue.

Separation of the group of probes bound to the targets from probes that are free of targets after contacting the sample solution with the probes can be carried out by binding the targets to a substrate surface before contacting the targets with the probes and separating the substrate bound to the target that also binds to a probe from probes that are in excess and do not bind to the targets which remain in solution. Alternately, the probes and sample solution can be contacted and a substrate included where probes that have not bonded to targets are bound to the substrate surface, and separating the substrate from probes bound to targets that remain in solution.

The step of measuring a parameter can be measuring a concentration of ions in a signal moiety solution by atomic absorption spectroscopy or by mass spectroscopy. The presence of the target in the sample solution can be calculated using values for an average size of the nanoparticles and an average number of bioreceptors attached to a probes. In one embodiment the presence can be determined quantitatively where calculations are performed using a value for the parameter of the signal moiety solution where probes bound to targets are broken down. In another embodiment the concentration of targets in the sample solution can be calculated by the difference in the number of probes contacted with the sample solution and the number or probes determined from the parameter of the signal moieties from the braking down of probes in the separated group of probes that did not bind to targets in the sample solution.

A system for determining the presence of biomolecule targets includes a vessel where a sample solution suspected of containing the targets and a plurality of bioreceptor functionalized nanoparticle probes and a solid substrate for selectively binding targets-probe conjugates or target free probes is contained. Target-probe conjugates form and a solid substrate bound with either to a target-probe conjugates or target free probes, and a complementary solution forms. The system also includes a separation device to separate the complementary solution from the substrate. The system also includes a reagent for breaking down the nanoparticles of the probes of either the probes attached ultimately to the substrate or the probes in the complementary solution where the reagent causes the formation of signal moieties from the nanoparticles of the probes. Both groups of probes, those with and those without bound targets can be separately mixed with reagents and broken down to signal moieties. The system also includes a device to measure a parameter of the solution or solutions of signal moieties. The substrate can be in the form of a plate or particles. The separation device can be a filter, chromatography column, or centrifuge. The reagent to form the signal moieties can be an oxidizer in solution when the nanoparticles are metal to form metal ions as signal moieties. The parameters can be measured using an atomic absorption or a mass spectrometer.

BRIEF DESCRIPTION OF THE DRAWINGS

A fuller understanding of the present invention and the features and benefits thereof will be obtained upon review of the following detailed description together with the accompanying drawing, in which.

DETAILED DESCRIPTION

Figure 1:
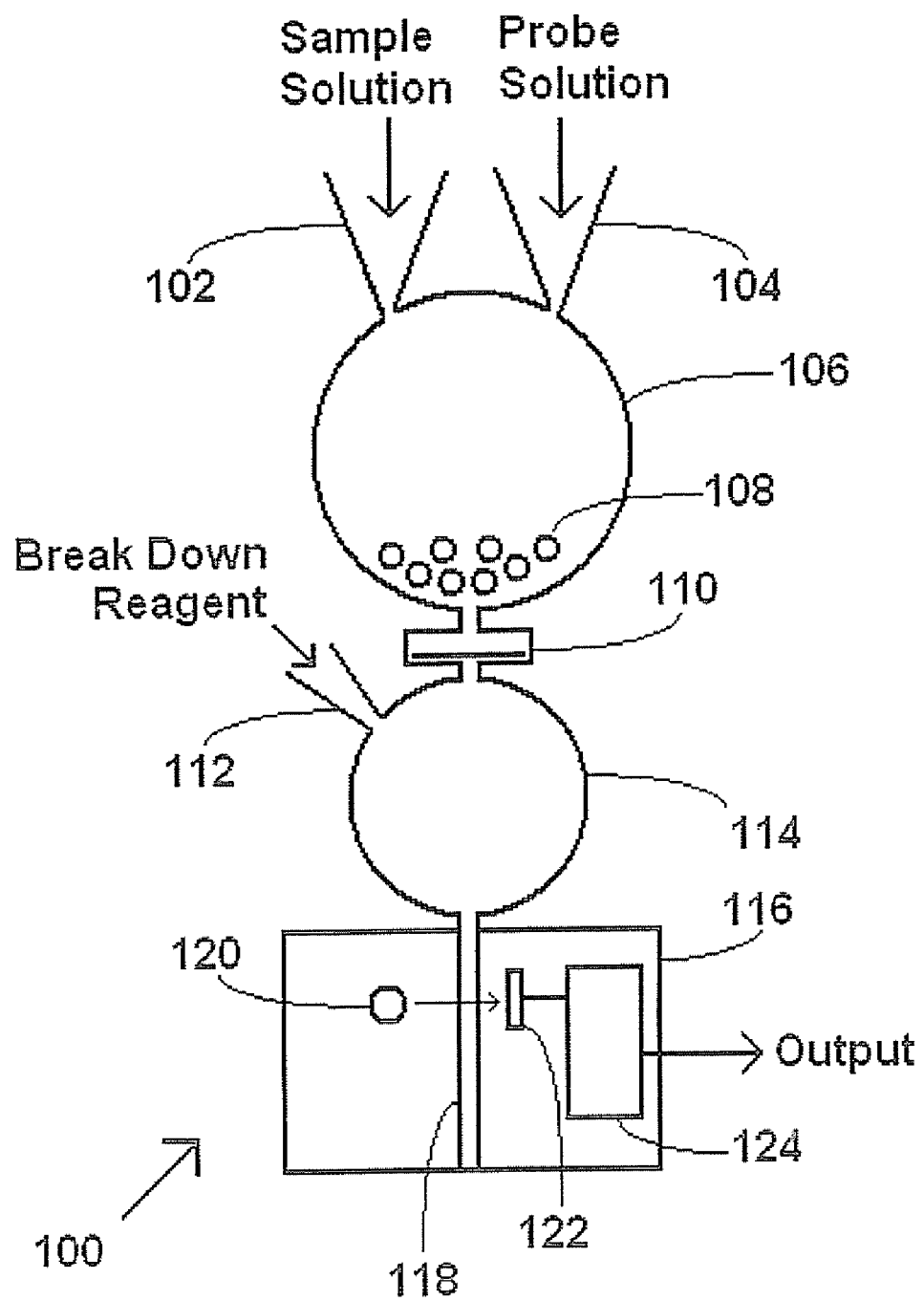
FIG. 1 is a schematic of a system of determining the presence of biomolecule targets according to an embodiment of the invention.

An ultra sensitive method for detection of target biomolecules includes the step of providing a plurality of bioreceptor functionalized nanoparticle probes. The nanoparticles can comprise metal, semiconductor, radioactive isotope or fluorescent dye molecules. The bioreceptors are adapted for binding to a target biomolecule. Binding can be covalent bonding, ionic bonding, complexation, hydrogen bonding, dipole-dipole interaction, van der Waals forces or any combination of such associations between at least one site of the target and at least one site of the bioreceptor as long as the binding is sufficiently strong to essentially form a target-probe associate with essentially complete binding of the targets where binding is maintained during any separating, washing or other steps of isolation of target-probe moieties during the method. A sample solution suspected of including the target is contacted with the probes, wherein if present, the target binds to the bioreceptor.

Such a bioassay can be carried out in a fashion employed in enzyme-linked immunosorbent assays (ELISA) or DNA chip multi-array analysis. In one embodiment, the method comprises the association of the target to a substrate surface fixed second bioreceptor followed by introduction of an excess of probes with subsequent separation of substrate fixed targets bound to the probe from probes free of the target. In another embodiment the targets are bound to probes in a solution containing excess probes followed by fixing probe bound targets to a substrate surface with fixed bioreceptor and subsequent separation of substrate fixed targets bound to the probe from unbound probes. In another embodiment of the invention a solution of target bound probes and excess probes are contacted with a substrate surface fixed target such that excess probes can be bound to the surface but target bound probes in solution can be removed from the excess probes bound to the substrate. The substrate fixed target can be the same or different than the target analyte but the relative binding constants of probes to the target analyte and to the substrate bound target should not promote the debonding of the probe from the target analyte. The substrate can be a plate or a particle that can be readily isolated from or washed of a solution containing the probes. In all embodiments the separating step comprises separation of probes having the target bound thereto from probes not having the target bound thereto.

In one embodiment of the invention probes having the target bound thereto are subjected to a step of "breaking down" which can be decomposition to generate a plurality of moieties to provide a signal, also referred to as "signal moiety" and include ions, discrete radioactive isotopes or discrete fluorescent dye molecules to form a solution comprising a large plurality of metal ions, radioactive isotopes or dye molecules. A concentration of signal moieties in the solution is then determined and this information is used to determine the concentration of the target in the original sample solution. Amplification of the signal occurs when the signal provided by the signal moieties of the decomposed probe is significantly greater than that provided by the intact probe. In another embodiment of the invention, probes that were not bound to the targets are broken down and analyzed wherein the difference, the decrease, in a signal from that where none of the provided probe has been bound to the target is used to determine the presence or quantity of the target in the sample. In this manner the detection can be carried out well above the detection limits of the analytical technique and when the sensitivity of the technique is sufficiently high, small target concentrations can be determined by the difference in measurement.

Bioreceptor probes can include, but are not limited to, antibody, DNA, proteins including enzymes, cells or cell components, such as biometric probes. Biometric probes can include molecular imprint antibodies, DNA-based aptamers, and peptide nucleic acids (PNA). Bioreceptors can be any moiety known to associate strongly to the target biomolecule. In some embodiments of the invention the bioreceptor should also associate selectively to the target biomolecule. For example, an operable DNA (gene) probes can be based on the well known hybridization process of joining of a single strand of nucleic acid with its complementary probe sequence. The operation of an antibody probe can be through a more general binding process that does not involve hybridization.

Binding of various bioreceptors to solid surfaces, such as the surface of metal nanoparticles, is well known. For example, complexes between DNA and negatively charged gold nanoparticles have been studied for many years (See, for example, Mirkin et al., Nature 382:607-609 (1996); Alivisatos et al., Nature 382:609-611 (1996)). Many creative schemes have exploited gold nanoparticles covalently functionalized with DNA sequences to bind specific target DNA sequences, either for nano-assembly or for oligonucleotide sensing (See, for example, Elghanian et al., Science 277: 1078-1081 (1997); Taton et al., Science 289:1757-1760 (2000); Park et al., Science 295:1503-1506 (2002); Cao et al., Science 297:1536-1540 (2002); Maxwell et al., J. Am. Chem. Soc. 124:9606-9612 (2002); Dubertret et al., Nat. Biotech. 19:365-370 (2001); Sato et al., J. Am. Chem. Soc. 125:8102-8103 (2003); Mirkin et al., Nature 382:607-609 (1996); Alivisatos et al., Nature 382:609-611 (1996); Chakrabarti et al., J. Am. Chem. Soc. 125:12531-12540 (2003).

Targets are generally biochemical substances, such as proteins, metabolites, nucleic acids, biological species or living systems, such as bacteria, virus or related components which are generally at ultra-trace levels in samples provided. In the case of medical diagnostic applications, the sample solution can be derived from tissues (for example using biopsy), blood or other bodily fluids (such as urine or saliva).

In embodiments of the invention, ultra sensitive detection is provided by signal amplification resulting from the chemical decomposition of solid nanoparticles having targets bound thereto into ions. This amplification is referred to herein as "atomic or molecular amplification". The atomic or molecular amplification factor is essentially equal to the number of atoms or molecules in the nanoparticle. In one embodiment, atomic absorption spectroscopy such as graphite furnace atomic absorption spectroscopy (GFAAS) is used to determine the concentration of ions. Alternatively, inductive coupled-plasma mass spectroscopy (ICP-MS) or other types of mass spectroscopy, or other types of analytical techniques which allow sensitive detection of ions may also be used. In an alternate embodiment of the invention, the nanoparticles comprise fluorescent dye molecules which are released from the nanoparticles and their concentration determined by fluorescent spectroscopy. In yet another embodiment of the invention, the nanoparticles comprise radioactive isotopes which after release from the nanoparticles have their concentration determined by measuring the radioactivity of the solution.

As an example for an ion-based embodiment of the present invention, assuming the nanoparticles are 40 nm, gold, and spherical, if 100 copies of capture antibody-antigen-nanoparticle labeled detector antibody complexes are formed on the microtiter plate in a sandwich ELISA assay, the amount of gold ions released from the microtiter plate after decomposition is $2 \times 10^8$, corresponding to approximately $10^{-15}$ moles. If the amount of solvent used to decompose the gold nanoparticle is limited to 1-10 µL, the total concentration of gold ions in solution will be $10^{-9}$ to $10^{-10}$M (100 s to 10 s of ppt). This concentration is around or very close to the detection limit of GFAAS or ICP-MS.

The present method thus uses nanoparticles, for example metal nanoparticles such as gold, silver or other metals. The present invention is generally described herein with respect to gold nanoparticles, which act as a signal transducer to measure the concentration of biomolecule targets in solution. The procedure according to an embodiment of the invention is described with reference to FIG. 1. Gold nanoparticles in the nanometer size range (1 to 1,000 nm), such as the size range of 10-100 nm, are modified to be functionalized with a bioreceptor, such as antibody, DNA, proteins including enzymes, cells or cell components that will recognize and bind to the specific target biomolecules to be detected in a sample solution. The size of the nanoparticles should be known, or can be determined by methods including transmission electron microscopy (TEM), and is preferably in a narrow size range.

The mixing of the nanoparticles with the sample solution allows the biomolecule targets, if present, to bind with the gold nanoparticles. Once bound, the probes are referred to herein as "conjugated nanoparticles" or "target-probe conjugates". In one embodiment of the invention there can be an excess of nanoparticles relative to the target such that non-conjugated nanoparticles remain after the mixing step. In another embodiment of the invention no excess of nanoparticles relative to the target is used such that no non-conjugated nanoparticles remain after the mixing.

The conjugated nanoparticles can be separated from any non-conjugated nanoparticles through ultrafiltration, or other methods. Thus, only the conjugated nanoparticles will remain in solution. The number of target biomolecules bound per nanoparticle may be determined based on a particular type of nanoparticles and this number may be used as a calibration point for the real sample analysis. For example, if each nanoparticle includes a single bioreceptor probe, the conjugated nanoparticles will have a single target bound thereto.

In the case of metal or semiconducting nanoparticles, the conjugated nanoparticles are then chemically decomposed. For example, for gold nanoparticles, the conjugated gold nanoparticles can be treated with an iodine/potassium iodide solution. This solution will oxidize gold atoms into gold cations, gold (I) or gold (III), to form an ion comprising solution. The concentration of gold cations is preferably determined by atomic absorption spectroscopy. However, as disclosed above, alternatively, inductive coupled-plasma mass spectroscopy (ICP-MS) other types of mass spectroscopy, or other types of analytical techniques that allow sensitive detection of metal ions may be used. For nanoparticles which release radioactive isotopes and fluorescent dye molecules after suitable treatment, appropriate analytical techniques, such as radioactivity detection and spectroscopy methods, respectively, may be used for detection.

When the size and shape of a nanoparticle is known, the number of atoms per nanoparticle can be calculated. The number of radioactive isotopes or dye molecules that each nanoparticle contains may be obtained by standard radioactivity or chemical analysis. Using this number, the concentration of the conjugated nanoparticles can be deduced. Since the number of biomolecule targets bound to each nanoparticle can be determined in a calibration study, the concentration of the biomolecule targets in the sample solution may be calculated.

In one embodiment, the ability to detect the decomposed nanoparticles, for example metal nanoparticle depends on the minimal detectable quantity of that ion by a specific analytical technique. The embodiment of the invention using metal nanoparticles permits analysis by GFAAS to very low concentrations. Table 1, below, gives the potential detection limit using different nanoparticles. For example, the absolute mass detection limit of GFAAS for elemental gold is approximately 6 pg. This corresponds to a number of gold nanoparticles around $10^{-19}$ mol for gold nanoparticle with a 40 nm diameter. According to a one to one nanoprobe-antigen binding, the detection limit for biomarkers could reach $10^{19}$ mol, or approximately 100 fg/mL for a sample volume of 100 μL. When the nanoparticle size is further increased to 100 nm, each nanoparticle will contain about 30 million gold atoms, which means the detection limit can be further decreased. The sensitivity of GFAAS differs for different metals. Some metals such as silver and cadmium are much more sensitive than gold. The sensitivity of Cd is ten to one hundred fold more sensitive than gold. If CdSe nanoparticles are used as nanoprobes, the detection limit will be decreased further.

TABLE 1

The instrument sensitivity of GFAAS and calculated detection limit of the proposed atomic amplification assay using different types of nanoparticle nanoprobes

| | Detection limit in | Detection limit of atomic amplification assay in absolute number of biomarker when using a: | |
|---|---|---|---|
| Element | absolute mass (pg) | 40 nm nanoprobe | 100 nm nanoprobe |
| Au | 6 | 10,000 ($10^{-19}$ mol, or 100 fg/mL) | 1,000 ($10^{-20}$ mol, or 10 fg/mL) |
| Ag | 0.4 | 1,000 ($10^{-20}$ mol, or 10 fg/mL) | 100 ($10^{-21}$ mol, or 1 fg/mL) |
| Cd | 0.2 | 1,000 ($10^{-20}$ mol, or 10 fg/mL) | 100 ($10^{-21}$ mol, or 1 fg/mL) |

As noted above, the inventive method can be used to detect ultra low concentration of biomolecule targets in sample solution. For example, a 40 nm spherical gold nanoparticle solution with a concentration of $10^{-12}$ M (1 picomolar) where the nanoparticles are bound to biomolecule targets in a one-to-one ratio would be very difficult if not impossible to detect by current spectroscopic means. However, each spherical gold nanoparticle with a core diameter of 40 nm can yield about 2 million gold atoms per nanoparticle. Thus, the decomposition of the gold nanoparticles yields a gold cation concentration of 2 μm ($1 \times 10^{-12}$ M$\times 2 \times 10^6$). Such a concentration of gold ions can be easily and accurately detected by atomic absorption spectroscopy or other methods. The detection limit can be further lowered by the use of larger nanoparticles.

More specifically, the atomic or molecular amplification effect and the detection limit of the present invention are primarily determined by the following three (3) factors:

(1) the intrinsic binding affinity between the receptor and target molecules (for example antibody and antigen molecules, or the complementary DNA strands);

(2) the instrumental detection limit of the corresponding element; and (3) the size and size distribution of the nanoparticles.

Essentially, the ultimate detection limit of any bioassay is determined by the binding affinity of the receptor and target biomolecules. For example, different antibodies have different binding affinities for different antigens, generally varying from $10^9$ to $10^{12}$ M$^{-1}$. The affinity of the conjugated antibody to nanoparticles is also affected by the conjugation process.

The second limiting factor that can determine the detection limit and sensitivity of the bioassay method according to the invention is the intrinsic instrumental detection limit, such as GFAAS and ICP-MS. For ultra trace analysis of metal and metal ions, currently GFAAS and ICP-MS are the two most sensitive techniques. Although the detection limit of ICP-MS is generally 100-1000 times lower than GFAAS, currently commercial available ICP-MS are mainly configured for analysis of large volume of sample solution, typically a few mL. In contrast, a typical GFAAS requires the injection of a sample volume of 1-50 μL. From the aspect of sample volume, GFAAS is more attractive. Moreover, the invention can use microfluidic techniques for small volume sample analysis when the use of small volumes is necessary. Although small volume samples may be diluted for ICP-MS analysis, dilution imposes additional steps to carry out bioassays according to the present invention.

Other than the intrinsic binding affinity of antibody-antigen and any instrumental detection limit, a third factor that determines the detection limit of the proposed atomic amplification bioassay method is the size and size distribution of the nanoparticles. As noted above, a larger nanoparticle will lead to a larger atomic amplification effect, because each nanoparticle will provide a larger amount of metal or other ions per labeled nanoparticle. However, when the nanoparticle becomes larger, the conjugation with the target biomolecules can become complicated. Furthermore, Brownian movement of the nanoparticles in solution can affect the binding of biomolecules. For different nanoparticles, the number of metal or other atoms that each particle contains is determined by the chemical structure and crystalline structure of the nanoparticles as indicated in Table 2 below. By combining the instrumental detection limit and size of the nanoparticles used in the study, an estimate of the targeting detection limits of the proposed bioassay methods of one embodiment of the invention was calculated.

This invention is not only aimed at detection, but also quantitative analysis of biomarker and other biologically molecules of interest, at ultra low level concentrations. Because the nanoparticles synthesized using chemical methods are not generally monodispersed, there is a limitation on the accuracy of the analysis due to the growth of the standard deviation of the number of gold atoms present as the number of detected biomolecules increases. The growth in the standard deviation of the number of gold atoms present grows roughly as the square root of the number of detected biomolecules. An analysis was made of the statistical reliability of a sample size of 100 nanoparticles (corresponding to the detection of 100 biomolecules) with diameters of 40 nm and 100 nm. As shown in Table 3, below, the half-width of a confidence interval at the 99% accuracy level for a sample size of 100 nanoparticles of 40 nm with a size distribution of 10% is roughly 7.74 times the number of gold atoms in an individual nanoparticle. The comparable datum for a sample of 100 nanoparticles at 100 nm with a size distribution of 5% is 3.87. This means using a nanoparticle sample with an average diameter of 40 nm and a size distribution of 10%, the proposed bioassay method will not allow one to distinguish 100±7 particles (molecules), but can distinguish a sample that contains about 100 from 150 analyte molecules.

TABLE 2

Structural parameters, instrumental detection limit and estimated bioassay detection limit using different nanoparticles as probe materials.

| Nanoparticle | Size (diameter in nm) | Number of atoms per particle | Instrument detection limit (data from Perkin Elmer) GFAAS (ppb) | ICP-MS (ppb) | Estimated detection limit of the bioassay (in absolute number of biomolecules)* GFAAS (10 µL sample volume) | ICP-MS (10 mL sample volume) |
|---|---|---|---|---|---|---|
| Au | 40 | $2 \times 10^6$ | 0.15 | 0.001 | 10,000s | 100,000s |
|  | 100 | $3 \times 10^7$ |  |  | 1000s | 10,000s |
| Ag | 40 | $2 \times 10^6$ | 0.005 | 0.002 | 100s | 100,000s |
|  | 100 | $3 \times 10^7$ |  |  | 10s | 10,000s |
| CdSe | 40 | $6 \times 10^5$ | 0.002 | 0.0001 | 100s | 10,000s |
|  | 100 | $1 \times 10^7$ |  |  | 10s | 1,000s |

*The calculation considered different sample volumes used in typical GFAAS (10 µL) and ICP-MS (10 mL) analysis. The instrument detection limit used in the calculation was 10 times higher than the listed detection limit in the table to reflect the actual detection limits under usual lab settings. The low-end of the linear dynamic range typically should be ten times higher than the actual instrument detection limit. The calculation does not consider the biomolecular binding affinity limit.

TABLE 3

Statistical analysis of the proposed bioassay accuracy using a sample size of 100 nanoparticles.

| Average Size nm | Distribution Size nm | Average Size # of Atoms | Distribution Size # of atoms | Half width of 99% confidence interval |
|---|---|---|---|---|
| 40 nm | 40 ± 4 nm (± 10%) | 2E8 ± 6E6 | 2E6 ± 6E5 (± 30%) | 1.548E7 (7.74 particle) |
| 100 nm | 100 ± 5 nm (± 5%) | 3E9 ± 4.5E7 | 3E7 ± 4.5E6 (± 15%) | 1.161E8 (3.87 particles) |

To establish an accurate bioassay method for extremely low level detection of biomolecules (around or less than 100 biomolecules immobilized on the microtiter plate), the dispersion of the nanoparticle size should be well controlled. Ultracentrifugation, chromatography, or fractional precipitation can be used as needed to increase the monodispersity of the particle size to increase accuracy. For the detection of biomolecules at concentration between femto ($10^{-15}$ M) to attomolar ($10^{-18}$ M) range, currently available nanoparticles can be used. The more monodispersed nanoparticle inherently gives the greater accuracy for any given nanoparticle size. The detection limit of the bioassay using, different instrumentation (GFAAS versus ICP-MS) and different sized nanoparticles can be roughly estimated; however detection limits must be examined and established during development of any specific assay.

Bioassays according to an embodiment of the invention can be based on microfluidic devices. Microfluidic devices permit low sample consumption in the sample analysis. In addition, microfluidics offer advantages including high surface area-to-volume ratio, fast mass and heat transfer and improved local control. A high surface area-to-volume ratio is important for reducing the amount of bioreagents used for the bioassays and improve the binding efficiency between biomolecules such as antibody-antigen interactions.

This present method is easy to conduct, accurate, and affordable. The method can be used by medical labs in hospitals and clinics for diagnosis of disease such as cancer, at early stages. The method may be used by research labs as a detection tool to study molecular biology and cellular biology. Some exemplary applications for the present invention are described below.

Early screening of prostate cancer by the measurement of Prostate Specific Antigen (PSA) level in blood can be carried out with detection at lower levels using the atomic amplification effect provided by the current invention. The invention can be applied to measurement of other serum biomarkers, such as PSCA, which are found in significantly lower concentrations in serum than that of PSA, prohibiting the potential use of this target by currently used immunohistolochemistry (IHC) and flow cytometry techniques.

The most common methods to detect the cancer biomarkers for breast cancer include IHC, fluorescent in situ hybridization (FISH) and ELISA. Among all the biomarkers, HER-2/neu is the most important biomarker for breast cancer diagnosis, and detection of HER-2/neu using IHC and FISH is approved by the FDA. The inventive approach can circumvent many of the current analytical arising from sample consumption and high minimal detection limits. The HER-2/neu protein can be used as a target protein for assay using the method of the present invention. Other tumor biomarker related to breast cancer can also be assayed by the inventive method.

The early detection of lung cancer is a problem that requires improved and more sensitive analytical techniques such as the amplification method of the present invention. Table 3 includes a list of lung cancer biomarkers that can be used as targets with the amplification method for embodiments of the present invention and includes the antibody clones that can be conjugated with the nanoparticies of the probe and bind to the biomarker.

TABLE 3

Lung cancer biomarkers and their relative antibodies

| Biomarker | Antibody clone |
|---|---|
| CA125 | OC125 |
| VEGF | Ab array |
| sIL-2R-alpha | Ab array |
| MIF | hMIF (12302) |
| CDC6 | 37F4 |
| Cytokeratin 7 | OV-TL 12/30 |
| Cytokeratin 8 | 35βH11 |
| Cytokeratin 18 | DC10 |
| Cytokeratin 19 | RCK 108 |
| ER-beta | N-19 |
| ER alpha | D-12 |
| Osteopontin | Anti-Human O-17 |
| γ-histone H2AX | p-H2A.X (Ser139) |

In an embodiment of the invention, the nanoparticles synthesized contain surface carboxylic acid groups, and amide coupling using EDC/NHS can be used to conjugate antibody to the nanoparticles. The conjugated nanoprobes can be purified by centrifugation or size exclusion chromatography to eliminate unconjugated antibody, streptavidin, or other chemical reagents.

Although the present invention has been described above for ultra sensitive bioassays for the detection and quantitative analysis of cancer-related biomarker molecules, it is clear that the methodology can be applied for other biologically relevant molecules, as well as viruses and organisms. Gold nanoparticles have been used as a contrast agent for tracing the location of proteins in biological cells using electron microscopy, however, revealing only qualitative information and not the amount of the target proteins in a cell. By decomposing the gold nanoparticles attached to the proteins and analyzing the gold ion concentration according to an embodiment of the invention, one can obtain quantitative information on the protein in a sample.

A system for carrying out the inventive method to determining the presence of biomolecule targets can be constructed having a vessel where a sample solution suspected of containing the targets can be combined with a plurality of bioreceptor functionalized nanoparticle probes. The vessel has a solid substrate to permit the separation of probes bound to targets from probes free of targets. In one embodiment of the system a substrate for selectively binding targets-probe conjugates is included. In another embodiment of the invention the included substrate can selectively bind target free probes. The vessel can have the substrate present before introduction of the sample solution and the probes or it can be introduced after contacting the probes with the sample solution. The substrate can be a surface of a plate or a particulate material where in one embodiment of the invention the surface of the substrate has moieties for selective binding with the target biomolecule and ultimately a target-probe conjugate. In another embodiment of the invention the surface has moieties for selectively binding to probes that are not conjugated with the targets. In one embodiment of the invention the vessel can be the substrate in a plate form.

The system also includes a separation device to separate the substrate from the remaining complementary solution of unbound probes, which are either free probes or target-probe conjugates. In one embodiment the device can be a holder for a plate substrate such that the complementary solution can be washed from the substrate bound to the target-probe conjugate. In another embodiment the separation device can be a filter where the complementary solution can be filtered from the particulate substrate. In other embodiments the separation device can be a centrifuge or a chromatography column.

The system also includes a reagent for breaking down the nanoparticles of the probes to generate the signal moieties that allow the ultimate analysis to occur with amplification from one given signal from a single target to a plurality of signals that can be related to the presence of a single target. The probes to be broken down can be either of or both of the groups of probes attached ultimately to the substrate or probes in the complementary solution. An exemplary reagent is an oxidizing reagent for the conversion of metal nanoparticles into a plurality of metal ions. In one embodiment of the invention both groups of probes, those with and those without bound targets can be separately broken down with reagents to generate signal moieties.

The system also includes a device to measure a parameter of the solution or solutions of signal moieties. For example, the device can be a spectrometer such as an ICP-MS or GFAAS. The system can be adapted to detect a plurality of targets simultaneously by the inclusion of a plurality of probes for the plurality of targets. A plurality of substrates for selective binding the plurality of probes or target-probe conjugates can be included in the system. For example two plates can be included in a vessel where the two plates selectively bind to two different target-probe conjugates or where one target is present and one plate binds to target-probe conjugates and the other plate binds to target free probes. In another embodiment of the invention different probes can have different nanoparticles with the same or different bioreceptors for different targets where the different nanoparticles can be simultaneously broken down to simultaneously detect different signal moieties. For example, one probe can have a gold nanoparticle and a second can have a silver nanoparticle with different bioreceptors so that upon oxidation to the signal moieties gold ions can indicate the presence or concentration of one target and silver ions can indicate the presence of a second target.

FIG. 1 illustrates a conceptual system of an embodiment of the invention where the components of the system are physically connected. Embodiments of the inventive system do not require that the components be physically linked together or be of the type inferred in FIG. 1. Various types of components of the system can be used and solutions and solids can be transferred between components manually or in an automated fashion, which is not illustrated. In FIG. 1 the system 100 of one embodiment of the invention includes a vessel 106 where a particular substrate 108 is mixed with a sample solution and a probe solution or suspension through ports 102 and 104. In other embodiments only one means of entry to the vessel is required. After the sample solution, probes and substrate 108 have been combined for a sufficient period of time for the target-probe conjugate and the binding of either the conjugate or the free probes to form in vessel 106, the bound substrate can be separated from the complementary liquid by the use of the separation device 110, which can be a filter as shown. As illustrated for system 100, the complementary solution flows into a second vessel 114 where a break down reagent can be introduced through port 112 to decompose the nanoparticles of the probe into the signal moieties and be in communication with a sample cell 118 of a device to measure a parameter 116, which for illustration purposes is shown essentially as an optical spectrometer where a light source 120 transmits light through the sample cell 118 to a detector 122 which sends an electrical signal to a processor or converter 124 to provide an output that can be interpreted by an individual assessing the results with respect to the presence or concentration of the target in the sample solution.

EXAMPLES

It should be understood that the Examples described below are provided for illustrative purposes only and do not in any way define the scope of the invention.

Example 1

Currently, GFAAS and ICP-MS are the two most sensitive techniques for ultra trace metal analysis. The detection limit of GFAAS was examined on gold nanoparticles. A citrate stabilized nanoparticles with an average core diameter around 35 nm were decomposed by a solution of $I_2$/KI, where the $I_2$ oxidizes gold atoms from the nanoparticles into gold ions. This solution was then diluted into four concentrations ranging from $10^{-11}$ to $10^{-15}$ M. This nanoparticle concentration range corresponds to a gold ion concentration ranging from $10^{-5}$ to $10^{-9}$ M. The analysis of 20 µL samples demonstrated that the lowest concentration of gold ions that can be detected by GFAAS is at the order of $10^{-8}$ M as analyzed using a Perkin Elmer AAalyst 600 instrument, resulting from a gold nanoparticle concentration of $10^{-14}$ M (10 s of femtomolar). Therefore, the minimal number of gold nanoparticles that can be detected by GFAAS is approximately 10,000.

Similar analysis was conducted on silver nanoparticles using ICP-MS technique. Citrate-stabilized silver colloids were purchased from Ted Pella, Inc. The nanoparticles were decomposed into silver ions using $I_2$/KI solution. Using ICP-MS technique, the lowest concentration of silver ions detected was 20 ppt, corresponding to a silver nanoparticle concentration of $10^{-16}$M.

Example 2

PSA is a 32 kDa single chain glycoprotein serine protease with a chymotrypsin like specificity produced by the secretory epithelium of the prostate gland. PSA that is normally secreted into the seminal fluid plays a functional role in the cleavage of the seminal vesicle proteins and the liquefaction of the seminal coagulum. Only low levels of PSA are normally present in the blood stream, and increasing serum concentrations indicate prostatic pathology, including benign prostatic hyperplasia and cancer of the prostate. Determination of PSA is now widely used for detection and management of patients with prostatic cancer and considered as the superior serological marker for cancer of the prostate. The atomic amplification assay approach was used to examine the detection of PSA and compared the results with standard ELISA assay.

A commercial ELISA kit for PSA assay along with a paired detector antibody was purchased from AnoGen, Inc. We conducted PSA assay using the ELISA kit and obtained a linear calibration curve. This assay kit uses horseradish peroxidase as the detector antibody label. The detector antibodies were labeled using the citrate-stabilized gold nanoparticles.

Citrate-stabilized gold nanoparticles with an average diameter of 40 urn were synthesized according to Turkevich et al. *Discuss. Faraday Soc.,* 11 (1951) 55. The size distribution of the nanoparticles was determined by transmission electron microscopy to be 43±3.5 nm, with a size distribution around or less than 10%. According calculations from this laboratory, Liu et al., *Colloids and Surfaces B: Biointerfaces,* 58 (2007) 3-7, the number of gold atoms in each particle is around 2 million.

The labeling was conducted according to the following procedure. An excessive amount of antibody (100 fold excess of antibody versus gold nanoparticle) was mixed with gold nanoparticles and incubated at room temperature for one hour. Unlabeled antibodies were then separated from labeled conjugate using size exclusion chromatography. The concentration of the labeled gold nanoparticles was determined by UV-Vis absorption spectroscopy and calculated according to the solution absorbance using an equation developed in Liu et al.

Figure 2:
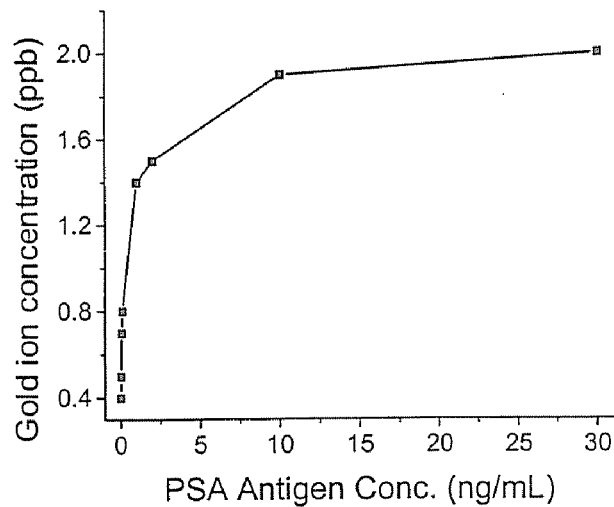
FIG. 2 is a plot of gold ion concentration formed from the amplification assay according to an embodiment of the invention where the target PSA, in concentrations from 0.01 to 30 ng/mL, was contacted with bioreceptors conjugated to gold nanoparticles with ions analyzed by GFAAS.
Figure 3:
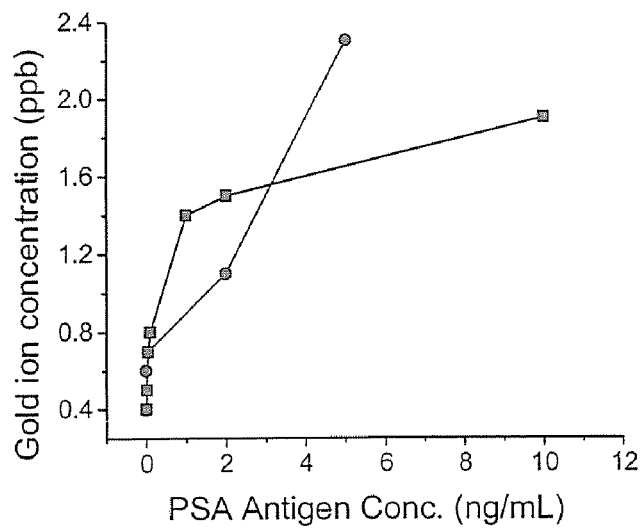
FIG. 3 is a plot of two different series of assays of PSA using the amplification assay according to an embodiment of the invention, using bioreceptors conjugated to gold nanoparticles with ions analyzed by GFAAS.

The ELISA assay using the gold nanoparticle conjugated detector antibody followed the same procedure as typical ELISA assay. After antigen binding and washing cycles, the gold nanoparticles were decomposed using 2 mL $I_2$/KI solution and the gold ion concentration was analyzed by GFAAS. FIG. 2 includes plots of gold ion concentration versus PSA concentration obtained from different assays. Results showed that the atomic amplification assay can detect PSA at concentration as low as 10-100 pg/mL. According to the volume of PSA antigen solution used for the assay (100 µL), and sample injection volume for GFAAS analysis (20 µL from the 2 mL of prepared solution), it is calculated that the AAA assay can detect PSA in the absolute mass of range 0.02-0.2 pg, corresponding to approximately $10^{-18}$ to $10^{-19}$ mol of PSA which is the detection limit calculated and given in Table 1. Furthermore, a linear relationship exists between gold ion and PSA in the concentration range of 10-1000 pg/mL. FIG. 3 is a plot of two different series of assays conducted in two different laboratories using PSA antibody and assay plates from two different commercial sources. From this comparison, one can see that the reproducibility of the results is fairly good even though no effort was made to optimize bioassay conditions and atomic absorption analysis parameters.

Example 3

Figure 4:
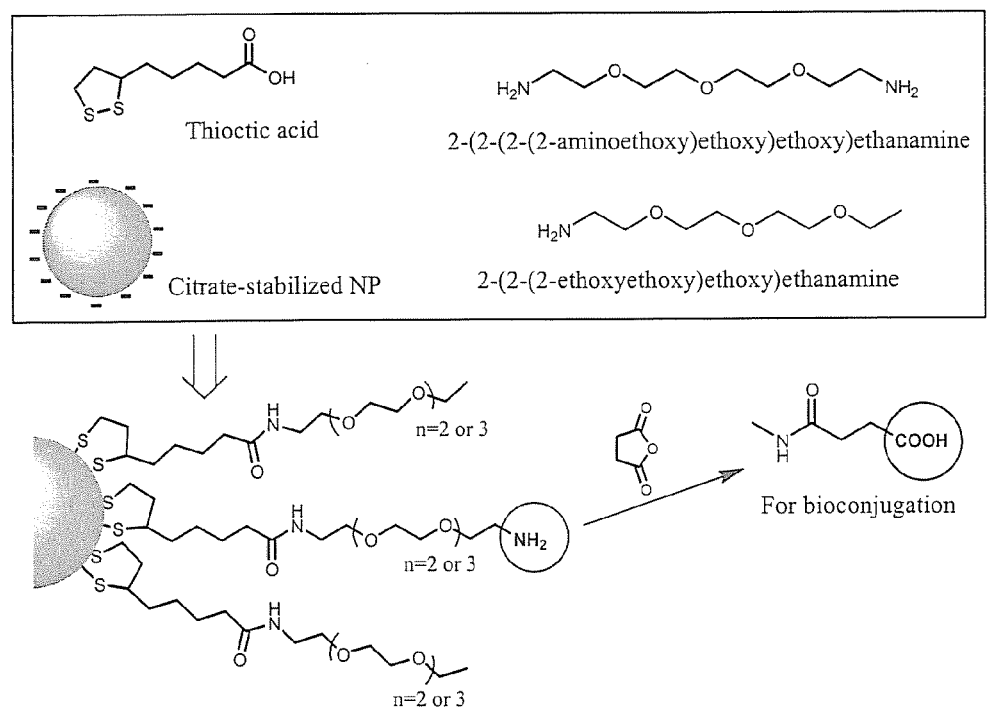
FIG. 4 is a reaction schematic for the preparation of a bioreceptor conjugated to gold nanoparticle according to an embodiment of the invention.

A route to nanoparticle probes according to an embodiment of the invention is given in FIG. 4. Relatively monodispersed citrate-stabilized gold nanoparticles can be synthesized using the method of Turkevich et al. in aqueous solution with sizes ranging from 10-120 nm, by controlling the volume of the capping ligand, tri-sodium citrate. The synthesis of citrate-stabilized silver nanoparticles can be done using by using silver nitrate as in Lee et al. *J. Phys. Chem.* 86 (1982) 3391. After purification, citrate-stabilized gold or silver nanoparticles will be converted to thioctic acid-protected nanoparticles through the ligand place exchange reaction. Two thiol groups-terminated thioctic acid is used to provide structural stability to the nanoparticles. The carboxyl groups on the nanoparticles are then activated with EDC (N-(3-dimethylaminopropyl)-N'-ethyl-carbodiimide) and NHS (N-hydroxysuccinimide). Two types of oligo(ethylene glycol) amine ligands, one with two amino end groups and one with a single amine end group, as shown in FIG. 4, are then coupled to the nanoparticles. The ratio of the two ligands can be adjusted to control the percentage of free amino groups modified on the nanoparticle surface. The free amino groups exposed on the nanoparticle surface will then be converted to carboxylic acid group by reaction with maleic anhydride. At this point, the nanoparticles can be couple with streptavidin or other detector antibody to prepare the conjugate probes.

Highly mono-dispersed CdSe nanoparticles can be synthesized at high temperature using $CdCO_3$ and selenium powder as key reagents, with TOPO (trioctylphosphine oxide) and stearic acid as surfactants. This method can be used to synthesize CdSe nanoparticles from 4 to 25 nm with good monodispersity (5%-10%). To improve the fluorescence quantum yield of those quantum dots and prevent them from photooxidation, a CdS shell layer can be deposited on the CdSe core surface as a passivation layer. This step can be done by slowly dropping a mixture solution of $(TMS)_2S$ (bis-trimethylsilane sulfide) and $Cd(CH_3)_2$ (dimethylcadmium) in TBP (tributylphosphine). A thiol ligand place exchange reaction can be used to substitute the original TOPO and stearic acid capping ligands with 2-mercaptosuccinic acid (MSA) ligand or thioctic acid. MSA-protected CdSe nanoparticles can then be converted to the probes using the route as illustrated in FIG. 4 for gold nanoparticles. Other methods can be used for the preparation of larger CdSe particles.

Example 4

PSA assay using quantum dot nanoprobes (QDs) was also carried out. Streptavidin-conjugated quantum dots with an average size of 5-8 nm were purchased from Invitrogen, Inc. An assay was conducted using an ELISA format and biotin-conjugated detector antibody and streptavidin QDs were added to conjugate with the detector antibody. The QDs bound to the microtiter plate were decomposed using a bromine solution. Decomposed QDs solution was then subjected to Cd ion analysis using an inductive coupled plasma mass spectrometer.

Figure 5:
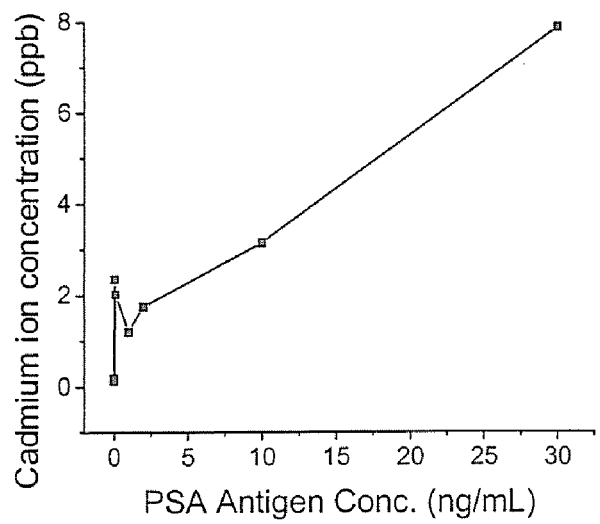
FIG. 5 is a plot of a series of amplification assays of 0.01 to 30 ng/mL PSA solutions according to an embodiment of the invention, using bioreceptors conjugated to quantum dots as nanoprobes with ions analyzed by ICP-MS.

FIG. 5 is a plot of Cd ion concentration versus PSA concentration. At ng/mL range, a linear relation was found from the PSA concentration versus Cd ion concentration. The QDs used in the current study have a core size of 5 nm. The amplification effect is limited to the order of 1,000 times less than a 40 nm gold nanoparticle. For the control sample with no PSA antigen present in the sample solution, a high level of Cd ion of 0.19 ppb was detected. The detection limit of the ICP-MS instrument used in this study for Cd ions is 0.001 ppb. The detected Cd ion level from the control sample is much above the instrumental detection limit indicating absorption of the Cd by the ELISA plate without the PSA target.

Example 5

Figure 6:
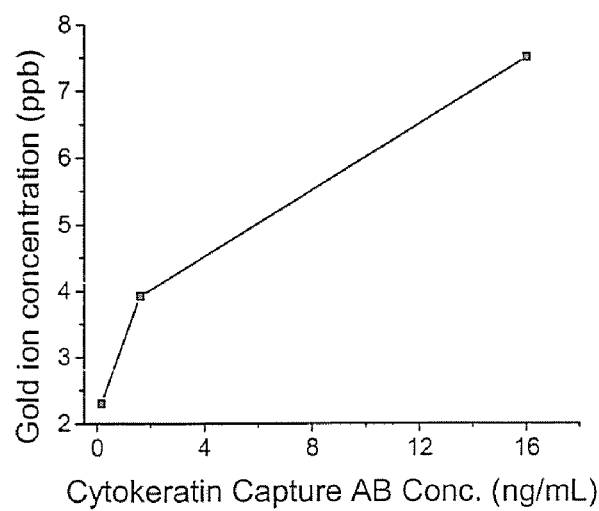
FIG. 6 is a plot of a series of amplification assays of cytokeratine from lysed cell samples of 0.16, 1.6, and 15 µg/mL according to an embodiment of the invention, using bioreceptors conjugated to gold nanoparticles.

Anti-cytokeratine antibody was conjugated to a 40 nm citrate-stabilized gold nanoparticle similarly to the conjugation of anti-PSA antibody as described above. An ELISA assay to detect cytokeratine from a lysed cell sample was conducted with these probes. Capture antibodies were immobilized on ELISA plates in three different concentration, 0.16, 1.6, and 16 µg/mL. The lysed cell samples were then added to the microwells of the plates. After incubation and washing cycle, antibody-gold nanoparticle conjugates were added to the plate in one concentration. The microtiter plate-bound gold nanoparticles were then decomposed using a 2 mL $I_2$/KI solution and the solution and subjected to gold ion concentration analysis. FIG. 6 is a plot of the measured gold ion concentration from the assayed samples versus capture antibody concentration. The plot clearly exhibits an increasing, although not linear, gold ion concentration with increased capture antibody concentration. Monoclonal anti-pan cytokeratine mixture of clones C-11, PCK-26, CY-90, KS-1A3, M20, A53-B/A2 (Sigma, MO) as the substrate bound antibody and monoclonal anti-cytokeratine 8, clone M20 (Sigma, MO) was used as the probe antibody.

This invention can be embodied in other forms without departing from the spirit or essential attributes thereof and, accordingly, reference should be to the following claims rather than the foregoing specification as indicating the scope of the invention. The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

We claim:

1. A method for detection of biomolecule targets, comprising the steps of:
   providing a probe solution comprising a plurality of probes comprising bioreceptor functionalized nanoparticles, wherein said nanoparticles consisting of a plurality of metal atoms, and wherein said bioreceptor is adapted for binding said probes to said targets;
   contacting a sample solution suspected of including said targets with said probe solution comprising said plurality of probes, wherein said targets when present in said sample solution bind to said plurality of probes;
   separating said plurality of probes into a first group of probes having said targets bound thereto and a second group of probes not having said targets bound thereto;
   breaking down said nanoparticles associated with probes in at least one of said groups of probes, wherein a plurality of signal moieties are released for each of said nanoparticles that are broken down to form at least one signal moiety solution;
   measuring a parameter of said signal moieties in said at least one signal moiety solution; and
   determining a presence of said targets in said sample solution from said parameter of said signal moieties.

2. The method of claim 1, wherein said signal moieties comprise ions, discrete radioactive isotopes or discrete fluorescent dye molecules.

3. The method of claim 1, wherein said breaking down step comprises oxidizing said plurality of metal atoms into metal ions.

4. The method of claim 3, wherein said metal atoms are selected from the group consisting of gold, silver, cadmium and an alloy thereof.

5. The method of claim 1, wherein said bioreceptor comprises at least one selected from the group consisting of antibody, DNA, proteins including enzymes, cells or cell components.

6. The method of claim 1, wherein said target comprises at least one biomarker of at least one type of cancer.

7. The method of claim 1, wherein said sample solution comprises a bodily fluid or a fluid derived from body tissue.

8. The method of claim 1, wherein said step of separating comprises binding said targets to a substrate surface before contacting said targets with said probes and separating said substrate from said probes not having said target bound thereto, wherein said probes not having said target bound thereto are in solution.

9. The method of claim 1, wherein said step of separating comprises binding said probes not having said targets bound thereto to a substrate surface after contacting said targets with said probes and separating said substrate from said probes having said target bound thereto, wherein said probes having said target bound thereto are in solution.

10. The method of claim 1, wherein said step of measuring a parameter comprises measuring a concentration of ions in said signal moiety solution by atomic absorption spectroscopy.

11. The method of claim 1, wherein said step of measuring a parameter comprises measuring a concentration of ions in said signal moiety solution by mass spectroscopy.

12. The method of claim 1, wherein said determining a presence of said target in said sample solution comprises calculations using values for an average size of said nanoparticles and an average number of said bioreceptors attached to each of said probes.

13. The method of claim 12, wherein said determining the presence comprises calculations using a value for said parameter of said signal moieties wherein said signal moiety solution results from breaking down said probes having said target bound thereto.

14. The method of claim 12, wherein said determining the presence comprises calculations using a value for said parameter of said signal moieties wherein said signal moiety solution results from breaking down said probes not having said target bound thereto and using a value for a concentration of said probes contacted with said sample solution.

* * * * *

UNITED STATES PATENT AND TRADEMARK OFFICE
CERTIFICATE OF CORRECTION

Page 1 of 1

PATENT NO. : 8,026,108 B1
APPLICATION NO. : 11/875252
DATED : September 27, 2011
INVENTOR(S) : Qun Huo, Xiong Liu and Qiu Dai It is certified that error appears in the above-identified patent and that said Letters Patent is hereby corrected as shown below:

In the specification,

Column 1, line 22, under

Statement Regarding Federally Sponsored Research or Development should read

This invention was made with Government support under Agency Contract DMR0552295 and DMI0506531 awarded by the National Science Foundation. The Government has certain rights in this invention.

Signed and Sealed this
Twenty-seventh Day of October, 2015

Michelle K. Lee
*Director of the United States Patent and Trademark Office*